(12) United States Patent
Hare

(10) Patent No.: US 7,743,778 B1
(45) Date of Patent: Jun. 29, 2010

(54) CANE WITH INTEGRAL URINATION AID

(76) Inventor: Clarence George Hare, Doylestown, PA (US); Christine Ann Byrne, legal representative, 25 Fairfield La., Doylestown, PA (US) 18901

( * ) Notice: Subject to any disclaimer, the term of this patent is extended or adjusted under 35 U.S.C. 154(b) by 0 days.

(21) Appl. No.: 12/429,693

(22) Filed: Apr. 24, 2009

(51) Int. Cl.
*A61H 3/02* (2006.01)
*A47K 11/12* (2006.01)

(52) U.S. Cl. .............................. 135/66; 135/68; 135/74; 4/144.1

(58) Field of Classification Search ............. 135/65–66, 135/68, 74; 248/155, 155.2–155.5; 4/144.1, 4/144.3, 144.4, 301; 604/329
See application file for complete search history.

(56) References Cited

U.S. PATENT DOCUMENTS

| | | | | |
|---|---|---|---|---|
| 1,120,305 | A * | 12/1914 | Graves | 135/68 |
| 2,311,049 | A * | 2/1943 | Hedden | 135/68 |
| 2,522,273 | A * | 9/1950 | Johnson | 4/144.1 |
| 2,678,054 | A * | 5/1954 | Bostelman | 135/68 |
| 2,778,370 | A * | 1/1957 | Chamblee | 135/68 |
| 3,070,807 | A * | 1/1963 | Wheeler | 623/28 |
| 3,074,420 | A * | 1/1963 | Gottman | 135/69 |
| 3,985,148 | A * | 10/1976 | Cadman | 135/66 |
| 4,060,859 | A | 12/1977 | Anderson | |
| 5,117,512 | A | 6/1992 | Bressler | |
| 5,282,599 | A * | 2/1994 | Arpaia et al. | 248/311.2 |
| 5,285,532 | A | 2/1994 | Sealy | |
| 5,331,689 | A | 7/1994 | Haq | |
| 5,647,519 | A * | 7/1997 | Brennan | 224/407 |
| 5,722,096 | A * | 3/1998 | Pfaeffle | 4/144.1 |
| 5,766,136 | A | 6/1998 | Cawood | |
| 5,875,499 | A | 3/1999 | Hoffman et al. | |
| 5,983,410 | A | 11/1999 | Webster | |
| 6,370,701 | B1 | 4/2002 | Siegrist | |
| 6,385,784 | B1 | 5/2002 | Donohue | |
| 6,385,785 | B1 | 5/2002 | Linden | |
| 6,401,263 | B2 | 6/2002 | Chang | |
| 6,543,064 | B1 | 4/2003 | Prall et al. | |
| 6,874,171 | B2 | 4/2005 | Erves | |
| 6,949,090 | B1 | 9/2005 | Leers et al. | |
| 6,968,577 | B1 | 11/2005 | Taft, Jr. | |
| 7,513,268 | B2 * | 4/2009 | Doman | 135/66 |

FOREIGN PATENT DOCUMENTS

| | | | |
|---|---|---|---|
| FR | 2675691 A1 | * | 10/1992 |
| JP | 09285510 A | * | 11/1997 |
| JP | 2000316925 A | * | 11/2000 |

* cited by examiner

*Primary Examiner*—Winnie Yip
(74) *Attorney, Agent, or Firm*—Caesar, Rivise, Bernstein, Cohen & Pokotilow, Ltd.

(57) ABSTRACT

A combined cane and urination aid for use by a male person is disclosed. The combination includes a cane having a support handle and at least two elongated support members extending downwardly therefrom. The support members are spaced apart along their length. The urination aid is retained between the elongated support members of the cane and includes a channel portion having an inlet end, a discharge end, and a length. The inlet end of the channel portion is shaped for receiving a flow of discharged urine. The channel portion conveys the flow away from the person so it may exit the discharge end of the channel portion at a sufficient distance to prevent splashed urine from reaching the person's body or clothes.

14 Claims, 2 Drawing Sheets

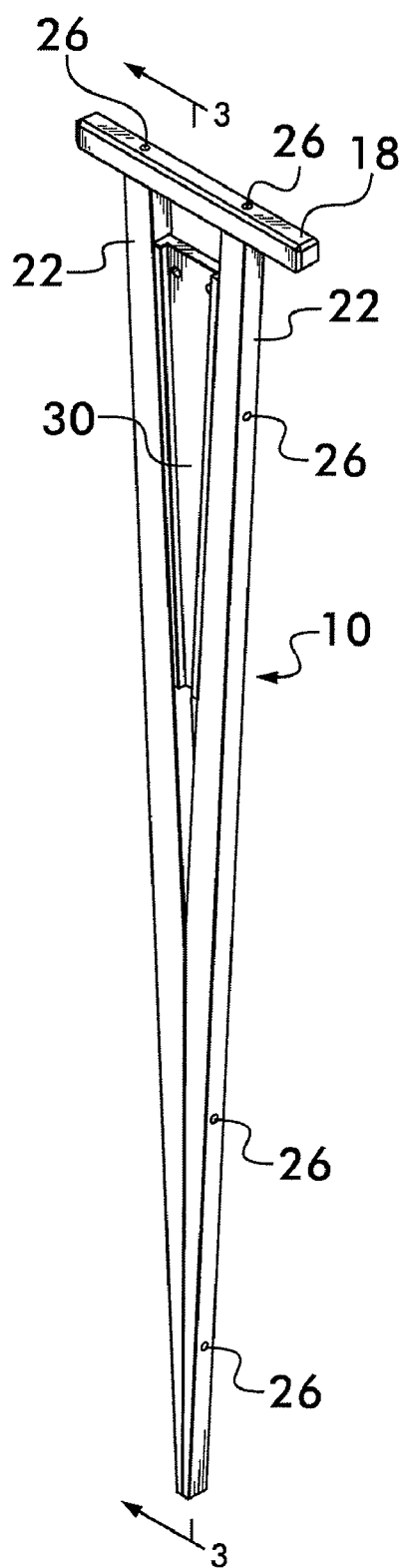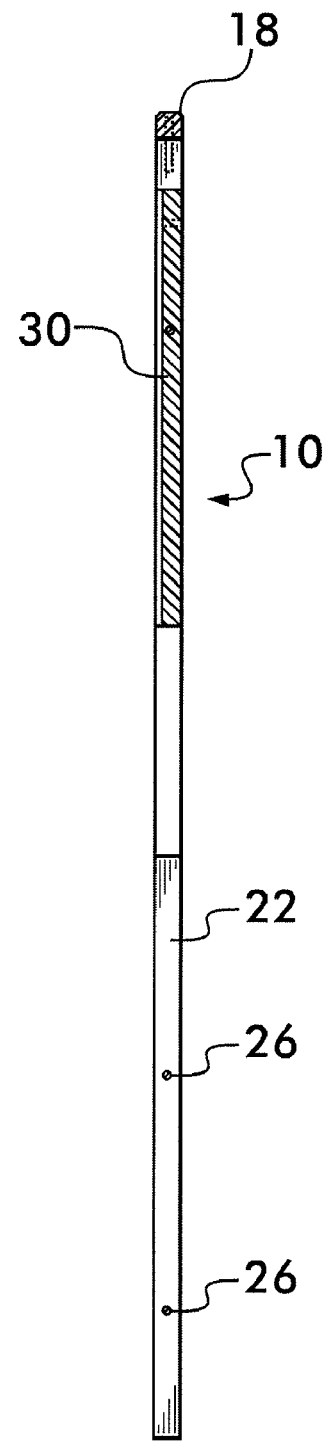
FIG.2
FIG.3

CANE WITH INTEGRAL URINATION AID

FIELD OF THE INVENTION

The present invention relates generally to an aid arranged for use during urination. More particularly, the present invention relates to a portable urination aid that is integrated into a cane and is arranged for use by a male person, such a hunter or an outdoorsman, during extended hunting or hiking trips in remote areas where bathroom facilities, such as toilets and urinals, are unavailable. The present invention prevents splashes that occur when urinating at such locations from reaching the body or clothes of the user.

BACKGROUND OF INVENTION

As long as an individual remains alive, there exists the need that the individual periodically relieve himself by urinating. Most often, individuals find themselves in close proximity to bathroom facilities, e.g., toilet or urinals. However, on occasion, individuals such as hunters and sportsmen, find themselves in locations such as large wooded areas or fields, where bathroom facilities are not in close proximity. In such circumstances, when the necessity to urinate arises, such individuals will often find a suitable location for urinating close by, such as against a tree or rock. Urination on trees, rocks or other objects having irregular surfaces, can often lead to urine splashes which frequently reach the individual's body and clothes, leaving an unpleasant and unsanitary condition which can lead to a potentially non-hygienic environment including increased germs and risk of disease. Sprayed urine, often caused by heavy winds, can also lead to these problems. Therefore, a device is needed that is economical, convenient and portable, and that when used, conveys urine a sufficient distance away from the user to prevent any splashing and sprays of urine from reaching the user's body or clothes.

The present invention relates to a cane including an integral urination aid for use when bathroom facilities are unavailable. The invention enables a user, such as a hunter, a hiker, or other outdoorsman, to convey the urine a sufficient distance from the user's body and clothes so that splashed or sprayed urine that has fallen from the discharge end of the urination aid does not reach the user's body or clothes. The present invention provides a urination aid which is simple, portable, hygienic, reliable in design and handling, and which allows for reuse without any required intermediate emptying. The present invention can be taken along and used on extended trips in the outdoors with optimum convenience.

SUMMARY OF THE INVENTION

A combined cane and urination aid for use by a male person is disclosed. The device includes a cane having a support handle and at least two elongated support members extending downwardly therefrom. The support members are spaced apart along at least a portion of their length. A urination aid is retained between the elongated support members and includes a channel having an inlet end, a discharge end, and a length. The inlet end is shaped for receiving a flow of discharged urine from a male person. The channel conveys the flow away from the person so it may exit the discharge end of the channel at a sufficient distance to prevent splashed urine leaving the discharge end of the channel from reaching the person's body or clothes.

BRIEF DESCRIPTION OF THE DRAWINGS

FIG. 2 is a perspective view of the cane with integral urination aid of the present invention showing the aid in the stowed position; and, FIG. 3 is a sectional view taken along line 3-3 of FIG. 2.

DETAILED DESCRIPTION OF THE INVENTION

Figure 1:
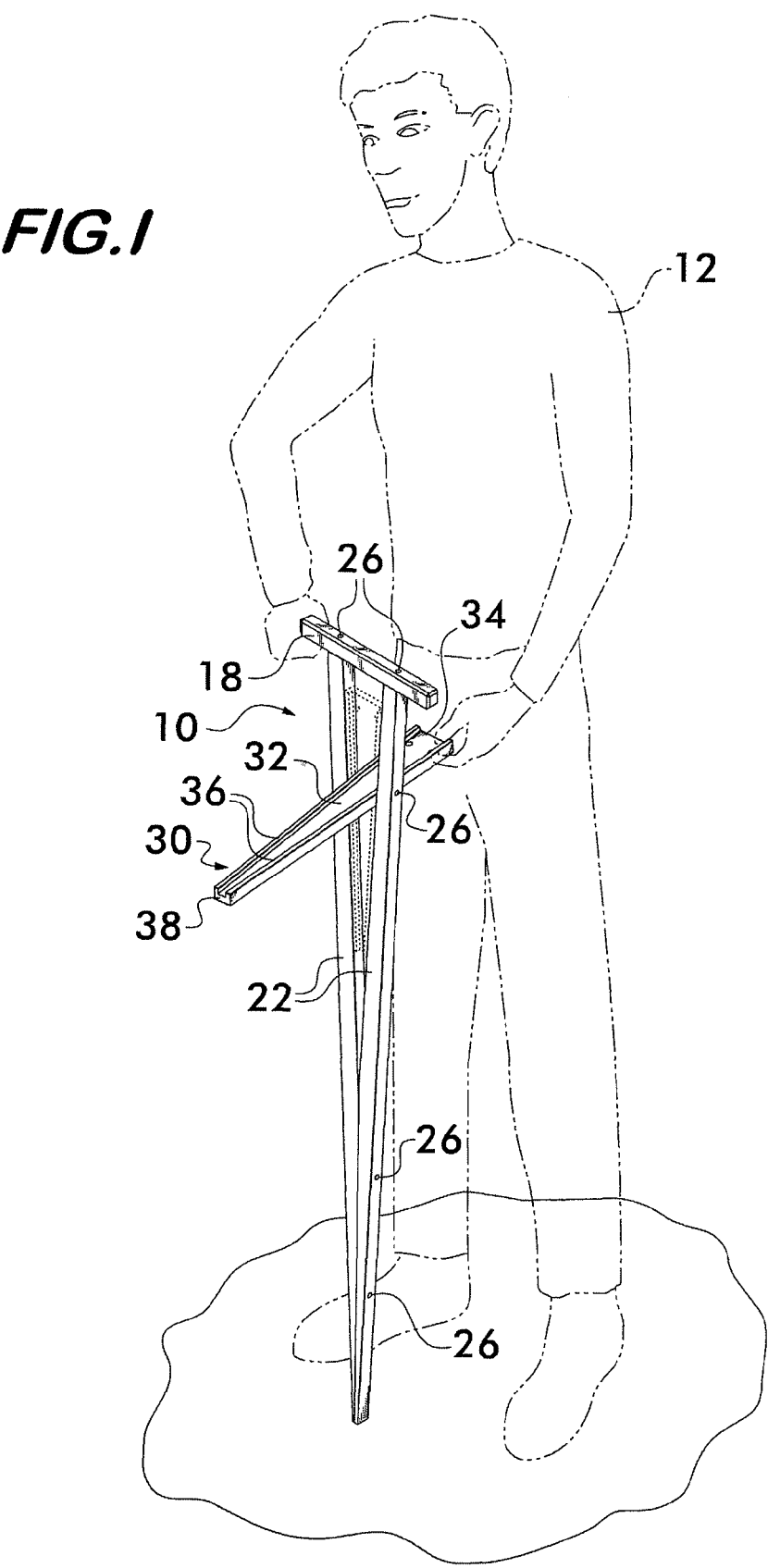
FIG. 1 is a perspective view of the cane with integral urination aid of the present invention, the urination aid being shown in the deployed position and being used by a person shown in phantom.

Referring now in detail to the various figures of the drawings wherein like reference characters refer to like parts, there is shown at 10 in FIGS. 1 through 3, an embodiment of the cane with the integral urination aid of the present invention. The embodiment 10 includes a cane handle 18 and two elongated support members or struts 22 attached thereto by any suitable means, e.g., flat-head wood screws 26. The handle 18 may include an optional pad (not shown) disposed thereover to provide some degree of padding and comfort to a user 12 during use. The handle 18 and struts 22 may be made of any suitable material, e.g., wood, plastic, or metal, and may include any suitable finish thereon, e.g., a stain or a clear polyurethane coating, to increase the aesthetic appeal of these components. The support members 22 extend downwardly from the handle 18 and are joined to each other at their lower portions by any suitable means, e.g., flat-head wood screws 26.

Located between the support members 22 at the upper portion thereof is a urination aid 30 which includes a flat bottom 32 and sidewalls 36 that extend upwardly therefrom to form a channel for containing urine as it is conveyed along the aid 30 from a wider inlet end 34 to a narrower discharge end 38. The urination aid 30 is of sufficient length to convey discharged urine away from the user such that any splashed or sprayed urine which has fallen from the discharge end 38 of the aid 30 will not reach the user's body or clothes. The urination aid 30 is mounted to the inside surfaces of the elongated support members 22 by any suitable means, e.g., flat-head wood screws 26. The height at which the urination aid 30 is located along the elongated support members 22 may be adjusted vertically to suit the user's particular anatomical requirements. As best shown in FIGS. 1 and 2, the urination aid 30 is arranged to pivot between a stowed position (FIG. 2) when not in use, and a deployed position (FIG. 1) to enable use. In this manner, when the urination aid 30 is in the stowed position, it is substantially parallel and coplanar with the elongated support members 22, thus enabling the embodiment 10 to be utilized as a conventional cane by the user, such as during a hunting or hiking trip. The urination aid 30 may be made of any suitable material, e.g., wood, plastic, or metal, and may include any suitable finish thereon, e.g., a stain or a clear polyurethane coating, to increase its aesthetic appeal.

As best shown in FIG. 1, when the need arises for the user to relieve himself by urinating and no bathroom facilities are available, such as during a hunting or hiking trip, the user simply pivots the urination aid 30 from the vertical stowed position (FIG. 2) to the substantially horizontal deployed position (FIG. 1) for receiving a flow of urine discharged from the body of the user 12. As best shown in FIG. 1, the user 12 may optionally grip the handle 18 to steady the device 10 during urination. In the deployed position, the urination aid 30 is tilted slightly off horizontal so that urine will flow downwardly from the wider inlet end 34 to the narrower discharge end 38. The urination aid 30 is of sufficient length to convey the urine a sufficient distance away from the user so that upon falling from the discharge end 38, the urine is a sufficient distance away from the user to prevent any splashed or sprayed urine from reaching the user's body or clothes.

The foregoing description and accompanying drawings should be considered as illustrative only of the principles of the invention. The invention may be configured in a variety of ways and is not intended to be limited by the preferred embodiments or methods. Numerous applications of the invention will readily occur to those skilled in the art from a consideration of the foregoing description. Therefore, it is desired that the invention not be limited to the specific example disclosed or the construction and operation shown and described. Rather, all suitable modifications and equivalents may be resorted to, falling within the scope of the invention.

I claim:

1. A cane with integral urination aid for use by a male person comprising:
   a. a cane having a support handle and at least two elongated support members extending downwardly therefrom, said support members being spaced apart along at least a portion of their length;
   b. a urination aid retained between said elongated support members, said urination aid including a channel portion having an inlet end, a discharge end, and a length therebetween, said inlet end being shaped for receiving a flow of urine discharged from the body of a male person, said length provided to convey said flow away from the person so it may exit the discharge end at a sufficient distance to prevent splashed urine from reaching the person's body or clothes.

2. The cane with integral urination aid of claim 1, wherein each said elongated support member includes an upper end and a lower end, said upper ends being joined to said handle, said support members being joined to each other at their lower ends.

3. The cane with integral urination aid of claim 1, wherein said elongated support members and said handle of said cane form a substantially triangular shape when viewed from the side of said cane, with an apex of said triangle facing downwardly.

4. The cane with integral urination aid of claim 1, wherein said channel portion includes a bottom and side walls extending upwardly therefrom.

5. The cane with integral urination aid of claim 4, wherein said bottom of said channel portion is flat.

6. The cane with integral urination aid of claim 4, wherein said bottom narrows as it extends from said inlet end to said discharge end.

7. The cane with integral urination aid of claim 6, wherein said side walls approach each other as they extend from said inlet end to said discharge end.

8. The cane with integral urination aid of claim 1 comprising a material selected from the group consisting of wood, plastic and metal.

9. The cane with integral urination aid of claim 1, wherein said urination aid pivots from a stowed position when not in use to a deployed position to enable use.

10. The cane with integral urination aid of claim 9, wherein when said urination aid is in said stowed position, it is substantially coplanar with said elongated support members.

11. The cane with integral urination aid of claim 9, wherein when said urination aid is in said deployed position, it is oriented substantially perpendicular to said elongated support members.

12. The cane with integral urination aid of claim 9, wherein when said channel portion is in said deployed position, it declines downwardly from said inlet end to said discharge end to permit the downward flow of urine therethrough and away from the person's body and clothes.

13. The cane with integral urination aid of claim 1, wherein said channel portion is imperforate.

14. The cane with integral urination aid of claim 1, wherein said urination aid is retained between said elongated support members by screws.

* * * * *